United States Patent [19]

Leichnitz

[11] 4,330,297
[45] May 18, 1982

[54] TEST TUBE CONSTRUCTION AND METHOD FOR MEASURING FOR NICKEL AEROSOLS

[75] Inventor: Kurt Leichnitz, Gross-Grönau, Fed. Rep. of Germany

[73] Assignee: Drägerwerk Aktiengesellschaft, Fed. Rep. of Germany

[21] Appl. No.: 192,550

[22] Filed: Sep. 30, 1980

[30] Foreign Application Priority Data

Oct. 23, 1979 [DE] Fed. Rep. of Germany ....... 2942674

[51] Int. Cl.³ .................... G01N 21/78; G01N 31/22
[52] U.S. Cl. ................................. 23/232 R; 422/60; 422/61; 422/86
[58] Field of Search ................ 422/55, 58, 59, 60, 422/61, 83, 86, 87, 88; 23/232 R

[56] References Cited

U.S. PATENT DOCUMENTS

| | | | |
|---|---|---|---|
| 2,908,555 | 10/1959 | Grosskopf | 422/86 |
| 3,022,141 | 2/1962 | Grosskopf | 422/60 |
| 3,985,017 | 10/1976 | Goldsmith | 23/232 R X |
| 4,271,125 | 6/1981 | Leichnitz | 422/60 X |
| 4,272,479 | 6/1981 | Huneke et al. | 422/86 X |

OTHER PUBLICATIONS

*The Merck Index of Chemicals and Drugs*—Seventh Edition, Merck and Co., N.J., 1960, pp. 132, 371 and 721.

*Primary Examiner*—Arnold Turk
*Attorney, Agent, or Firm*—McGlew and Tuttle

[57] ABSTRACT

A testing device for measuring for nickel-aerosols includes a glass tube having breakable end tips for opening the tube for the passage of a test gas therethrough and a filling in the tube which includes a closed ampoule of hydrochloric acid, a filter layer for entrapping nickel particles of the gas being tested, a reaction layer of a material impregnated with a color reagent for nickel, a granular buffer layer and a second breakable ampoule of ammonia water arranged in the direction of flow of the test gas through the tube. The testing is carried out by breaking the first ampoule to release hydrochloric acid which flows through the filter and reacts with the nickel particles which pass to the reagent layer, subsequently breaking the second ampoule so that its contents will be directed into the granular buffer layer and in the reagent layer. The ammonia water in the second ampoule is directed into the buffer layer and then into the reagent layer to produce a color reaction in the reagent layer and the intensity of the discoloration produced is proportional to the amount of nickel filtered out of the test gas. This color is compared with a standard showing the color of reaction for various concentrations of nickel.

8 Claims, 1 Drawing Figure

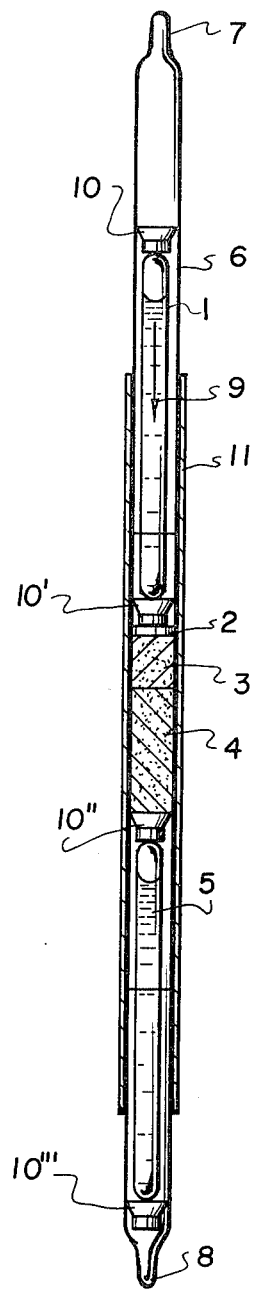

TEST TUBE CONSTRUCTION AND METHOD FOR MEASURING FOR NICKEL AEROSOLS

FIELD AND BACKGROUND OF THE INVENTION

This invention relates to testing apparatus and methods in general and, in particular to a new and useful apparatus and method for testing for nickel aerosols in a gas, such as air.

The only allowable low limit value of nickel dust in a workplace is 0.05 mg/m$^3$, according to MAK-Value-list 1979, which shows this dust to be a potential danger. Frequent and regular supervision of nickel aerosols in the air is therefore necessary to avoid health hazards.

A known method for determining nickel aerosols, employs a cellulose membrane filter for taking samples through which the gas to be tested is sucked with a pump. Then, in a first step, the organic filter material is dissolved in concentrated, warm nitric acid and the liquid is nearly completely evaporated. A mixture of concentrated nitric acid and perchloric acid is added to the remaining concentrate, and this mixture is then evaporated at a higher temperature (400° C.). After cooling, the residue is dissolved in thinned nitric acid. The nickel determination is performed from this solution in the oxidizing flame of an atomic absorption spectrophotometer.

The large equipment requirements of this process and the skilled personnel which is required are some of the disadvantages of this process. The performance is cumbersome and time-consuming and the test results are not readily available at the place of the sample-taking (NIOSH Manual of Analytical Methods, Second Edition, Volume 3, page 206).

In a known test tube with three or more separately disposed reagents or reagent layers, respectively, are one or more reagents or reagent layers, preplaced relative to an indicator layer, and positioned in one or more breakable ampoules. The testing tube itself is also breakable in the region of the ampoule and is provided there with a tubing cover. After breaking of the test tube, it seals the interior of the tube against the outside (See German Pat. No. 1,093,114).

SUMMARY OF THE INVENTION

The present invention provides a simple method and means for the determination of nickel aerosols, which can be performed and used without a great amount of preparation and without loss in time, even when using less qualified personnel, and which produces a result which is readily available at the test place.

In accordance with the invention, a testing device for measuring of nickel aerosols, includes a glass testing tube having sealed end tips which may be broken off to permit the flow of the test gas therethrough and which carries in the direction of flow a first ampoule filled with a hydrochloric acid, a filter layer which entraps nickel particles in the gas, a reaction layer of a material impregnated with a color reagent for nickel, a buffer layer after the reaction layer, a second breakable ampoule having ammonia water which may pass through the buffer layer and the reaction layer to produce a discoloration of the reaction layer in accordance with the nickel concentration, all being arranged in the direction of flow of the test gas in the testing tube.

The invention advantageously employs the test tube method. All of the necessary elements for testing are united in a test tube. The test tube method is universally known and allows, in a simple fashion, for example, the performance of the air testing for supervising the place of work. The test result is immediate and is readily available at the place of the test.

For the determination only in the first step, the test tube tips are opened and then the test gas is sucked through the testing tube and thereby through the filter layer with a known suction pump.

In an immediately following further work step, the ampoule is first broken and its contents are directed against the filter layer and to a reagent layer. Thereafter, an additional ampoule, located behind the reagent layer, is broken, and its contents are directed against the reagent layer. The reagent layer discolors in the presence of a nickel aerosol. The intensity of the discoloration is proportional to the measure of nickel deposited on the filter layer. It is possible to determine concentrations in the range of from 0.02 to 1 mg nickel per m$^3$, that is, in the range of the MAK value.

The buffer layer following the reagent layer assures a uniform distribution of the ampoule liquid, particularly after breaking of the ampoule located behind the reagent layer.

Accordingly, an object of the present invention is to provide a testing device for measuring for nickel aerosols which includes a test tube with first and second breakable ampoules containing a first reagent which flows past the filter which entrains the nickel particles from a testing gas to a reagent layer in the tube and another breakable ampoule having ammonia water which reacts with the reagent layer after passing through a buffer layer.

A further object of the invention is to provide a method of measuring for nickel aerosols in air which comprises passing the testing gas through a filter to entrain the nickel particles, directing a reagent against the filter to entrain the particles and react therewith and through a reagent layer to produce a reaction thereon along with a second reagent which is passed through a buffer layer and in the opposite direction to the first reagent from the ampoule to produce a color reaction on the reagent layer which is proportional to the nickel content of the particles.

Another object of the present invention is to provide a testing device for measuring nickel aerosols in air which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which a preferred embodiment of the invention is illustrated.

BRIEF DESCRIPTION OF THE DRAWING

In the drawing:

The only FIGURE of the drawing shows a sectional view of a testing device, constructed in accordance with the invention.

DESCRIPTION OF THE PREFERRED EMBODIMENT

Referring to the drawing in particular, the invention embodied therein, comprises, a testing tube 6, which is made of glass and includes end tips 7 and 8 which are breakable to open each end for the passage of a testing gas through the tube in the direction of flow indicated by the arrow 9.

The interior of the tube carries four separate spacers or stoppers 10, 10', 10'' and 10''', and between the first two spacers 10 and 10', there is a breakable ampoule 1 filled with hydrochloric acid which, when released, flows pass the stopper 10' through a filter layer 2 to react with any nickel particles thereon which may be entrained in the filter as a result of the passage of the testing gas therethrough.

A filter layer 2 is arranged between stoppers 10' and 10'', along with a granular reagent layer 3 which comprises a silica gel impregnated with a color reagent for nickel followed by a granular buffer layer 4. An ampoule 5 which is also breakable and contains ammonia water is located between stopper elements 10'' and 10''', and all of the stopper elements hold the relative materials in their orientation and against vibration, but permit flow completely through the tube.

Buffer layer 4 which follows reagent layer 3 assures a uniform distribution of ampoule liquid from the breakable ampoule 5 which is located downstream of the granular buffer layer 4. The outside of the glass tube is advantageously covered with a tubing cover 11 which is shrunk-fit thereover and holds the parts of the tubing together when various portions thereof are broken so as to break the ampoules 1 and 5.

A color reagent which is satisfactory toward detecting the presence of nickel quantities is benzildioxime, or cyclohexane-1,2 dione-dioxime. The material for the filter layer 2 is advantageously a glass fabric.

The color reagent which impregnates the silica gel in the granular reagent layer 3 is advantageously dimethyl-glyoxime. The material of filter layer 2 may also be an asbestos filter paper. Buffer layer 4 may advantageously comprise inert quartz.

The measurement is performed as follows in two working steps:

1. After breaking of the tips 7 and 8, the test tube is inserted in a known suction pump, and the gas to be tested is then sucked with 100 strokes in the stream direction into the test tube. Thereby, the suspended particles, including the nickel particles present in the test gas, are deposited in filter layer 2; and 2. At this moment, the ampoule 1 is also broken in the longitudinal axis with the glass tube 6. The hydrochloric acid is thrown in the direction of the filter layer 2. The hydrochloric acid dissolves the suspended nickel material and flushes it into the reagent layer 3. The ampoule 5 is then broken in the same manner, and the ammonia water is thrown through the buffer layer 4 into the reagent layer 3. There, the color reaction occurs. The intensity of the discoloration is proportional to the amount of nickel filtered out of the test gas. Comparing a color standard provided, the nickel concentration of the test gas to be determined results.

While a specific embodiment of the invention has been shown and described in detail to illustrate the application of the principles of the invention, it will be understood that the invention may be embodied otherwise without departing from such principles.

What is claimed is:

1. A testing device for measuring nickel aerosols comprising a glass tube; a breakable closure at each end of the tube which may be broken to open the tube for flow therethrough of a gas to be tested; in series within said tube a first breakable ampoule containing a quantity of hydrochloric acid, a filter layer adjacent said first ampoule which is constructed to remove nickel particles from the gas, a granular reagent layer of silica gel impregnated with a color reagent for nickel adjacent said filter layer, and a second breakable ampoule containing ammonia water adjacent said granular reagent layer; and a tubing cover closely-fitted and extended over the tube to hold the tube together upon breakage of said ampoules.

2. A testing device for measuring the presence of nickel aerosols, as claimed in claim 1, wherein said color reagent for nickel is benzildioxime.

3. A testing device for measuring the presence of nickel aerosols, as claimed in claim 1, wherein said color reagent for nickel comprises cyclohexane-1,2-dione-dioxime.

4. A testing device for measuring the presence of nickel aerosols, as claimed in claim 1, wherein said color reagent for nickel is dimethylglyoxime.

5. A testing device for measuring the presence of nickel aerosols, as claimed in claim 1, wherein the material for the filter layer comprises a glass fabric.

6. A testing device for measuring the presence of nickel aerosols, as claimed in claim 1, wherein said material for said filter layer comprises asbestos filter paper.

7. A testing device for measuring the presence of nickel aerosols, as claimed in claim 1, wherein said reagent layer is followed by a buffer layer of inert quartz in the flow direction.

8. A method of measuring the presence of nickel aerosols in a gas, comprising, directing the gas through a testing tube having a filter therein to entrain any nickel particles in the filter, breaking an ampoule of a first reagent material so that the reagent material flows into the filter, directing the reagent material with the entrained filter particles into a reagent layer, breaking a second ampoule to cause a second reagent to flow through a buffer layer and to the reaction layer and thereby causing a discoloration of the reaction layer, and comparing the discoloration of the reaction layer with a standard coloration for various percentages of nickel content in order to determine the nickel present in the gas.

\* \* \* \* \*